(12) United States Patent
Mäntylä

(10) Patent No.: US 9,625,382 B2
(45) Date of Patent: Apr. 18, 2017

(54) METHOD AND APPARATUS FOR MEASURING GLOSS

(71) Applicant: VALMET AUTOMATION OY, Espoo (FI)

(72) Inventor: Markku Mäntylä, Kangasala (FI)

(73) Assignee: VALMET AUTOMATION OY, Espoo (FI)

( * ) Notice: Subject to any disclaimer, the term of this patent is extended or adjusted under 35 U.S.C. 154(b) by 0 days.

(21) Appl. No.: 14/439,259

(22) PCT Filed: Oct. 30, 2013

(86) PCT No.: PCT/FI2013/051028
§ 371 (c)(1),
(2) Date: Apr. 29, 2015

(87) PCT Pub. No.: WO2014/068188
PCT Pub. Date: May 8, 2014

(65) Prior Publication Data
US 2015/0268166 A1  Sep. 24, 2015

(30) Foreign Application Priority Data
Oct. 30, 2012 (FI) .................................... 20126126

(51) Int. Cl.
| | |
|---|---|
| *G01N 21/55* | (2014.01) |
| *G01N 21/57* | (2006.01) |
| *G01N 21/47* | (2006.01) |
| *G01N 21/86* | (2006.01) |
| *G01N 21/89* | (2006.01) |
| *G01N 33/34* | (2006.01) |

(52) U.S. Cl.
CPC ............. *G01N 21/57* (2013.01); *G01N 21/47* (2013.01); *G01N 21/86* (2013.01);
(Continued)

(58) Field of Classification Search
CPC ........ G01N 21/57; G01N 21/47; G01N 21/86; G01N 21/8901; G01N 33/346;
(Continued)

(56) References Cited

U.S. PATENT DOCUMENTS

| | | |
|---|---|---|
| 3,636,361 A | 1/1972 | Bowers |
| 5,078,496 A | 1/1992 | Parker et al. |

(Continued)

FOREIGN PATENT DOCUMENTS

| | | |
|---|---|---|
| JP | 2009074981 A | 4/2009 |
| WO | 0157497 A1 | 8/2001 |
| WO | 2011042606 A1 | 4/2011 |

OTHER PUBLICATIONS

May 27, 2013 Search Report issued in Finnish Patent Application No. 20126126.

(Continued)

*Primary Examiner* — Tri T Ton
(74) *Attorney, Agent, or Firm* — Oliff PLC

(57) ABSTRACT

An apparatus of measuring a small scale property of a sheet, the apparatus includes: a first light source for illuminating the sheet moving with respect to the illumination; a detector for forming a total intensity of reflection of the light illuminating the moving sheet by each detection; a detected dimension of the reflection on the sheet in the direction of the movement being limited the same as or shorter than a lowest acceptable spatial resolution of the measurement; a duration of each detection being equal to or shorter than the lowest acceptable spatial resolution divided by a speed of the moving sheet; and a processing unit for forming information about a small scale variation of gloss of the sheet on the basis of the detections by the detector.

16 Claims, 7 Drawing Sheets

(52) U.S. Cl.
CPC ....... *G01N 21/8901* (2013.01); *G01N 33/346* (2013.01); *G01N 2201/062* (2013.01); *G01N 2201/069* (2013.01); *G01N 2201/06113* (2013.01); *G01N 2201/12* (2013.01)

(58) Field of Classification Search
CPC ... G01N 2201/06113; G01N 2201/062; G01N 2201/069; G01N 2201/12
USPC ................................................ 356/445–448
See application file for complete search history.

(56) References Cited

U.S. PATENT DOCUMENTS

| | | | |
|---|---|---|---|
| 5,162,660 | A | 11/1992 | Popil |
| 6,233,053 | B1 | 5/2001 | Preston et al. |
| 7,019,822 | B1 | 3/2006 | Doak et al. |
| 2002/0114494 | A1 | 8/2002 | Komulainen et al. |
| 2004/0107061 | A1 | 6/2004 | Ruuska |
| 2005/0150288 | A1 | 7/2005 | Typpoe et al. |
| 2006/0256341 | A1 | 11/2006 | Kuwada |
| 2007/0103688 | A1 | 5/2007 | Kuusela |
| 2008/0245979 | A1 | 10/2008 | Banton et al. |
| 2008/0252909 | A1 | 10/2008 | Honguh et al. |
| 2009/0097033 | A1 | 4/2009 | Kuusela |
| 2010/0296107 | A1 | 11/2010 | Keranen |

OTHER PUBLICATIONS

Jan. 23, 2014 International Search Report issued in International Patent Application No. PCT/FI2013/051028.

Nov. 12, 2015 Search Report issued in European Patent Application No. 13851514.

METHOD AND APPARATUS FOR MEASURING GLOSS

FIELD

The invention relates to a method and an apparatus for measuring gloss.

BACKGROUND

The following description of background art may include insights, discoveries, understandings or disclosures, or associations together with disclosures not known to the relevant art prior to the present invention but provided by the invention. Some of such contributions of the invention may be specifically pointed out below, whereas other such contributions of the invention will be apparent from their context.

Printed papers particularly those having a fairly dark single color on a large area may appear spotted or cloudy. Such a phenomenon is called mottling and it may be caused by various reasons such as bad formation, small scale variation of coating, uneven absorption of ink or the like. Irrespective of the physical reason, small scale variation of gloss of paper before printing is known to result in mottling in the printed paper.

Gloss is visual appearance of material such as paper, carton and board, and it has a close relation with surface texture. Surface gloss is conventionally measured as a specular reflection of visible light from a relatively large area in the order of at least tens of square millimeters. In addition to reflection from the surface, scattering from inside the object may also have some effect to the value of the measured surface gloss.

Lately, a measurement of micro gloss which is also measured as a specular reflection has become important particularly in paper industry. The micro gloss is a two-dimensional representation of a reflection of light from a small measured area, the area being from about a few square micrometers to tens of square millimeters. An idea of measuring micro gloss has been considered possible such that a camera with a detector of a matrix of pixels captures images of a moving surface which is illuminated with stroboscopic flashes. Because small area may be captured in the image, resolution in the order of 100 µm could be reached.

However, the measurement faces problems. For example, the captured image of the web is slightly inaccurate since the web is moving during exposure with the stroboscopic flashes. Moreover, the measurement configuration with a camera having a detector matrix, a stroboscopic flash light, and optical components is complicated. Hence, there is a need for better measurement of small scale gloss.

BRIEF DESCRIPTION

An object of the invention is to provide an improved solution for measurement of gloss.

According to an aspect of the present invention, there is provided an apparatus of claim 1.

According to another aspect of the present invention, there is provided a method of claim 15.

The present solution provides advantages. The variation of gloss can be measured easily and used for process control if found necessary.

LIST OF DRAWINGS

Embodiments of the present invention are described below, by way of example only, with reference to the accompanying drawings, in which FIG. 1A illustrates an example of the measurement configuration where a whole area of an illuminated spot is detected;

DESCRIPTION OF EMBODIMENTS

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments.

A small light spot is detected on a moving sheet in the measurement. The size of the spot determines at least partly the spatial resolution of the measurement. The smaller the detected spot is the better accuracy may be achieved. Since the sheet is moving, the spatial resolution in the direction of movement also depends on the speed of the movement and the time how long it takes to form one detection value. The shorter the time for a detector to output a value of detection, the more accurate result may be achieved.

Figure 1A:
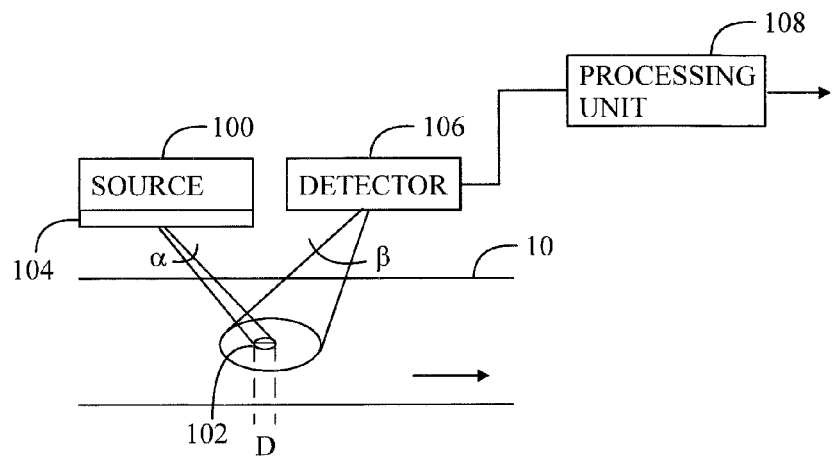
FIG. 1B illustrates an example of the measurement configuration where only a section of the illuminated spot is detected.
FIG. 1C illustrates an example of the measurement configuration where a detection is based on an integration over a time window.

FIG. 1A presents an embodiment of an apparatus of measuring a small scale property of a moving sheet 10. In general, the sheet 10 may comprise paper or cardboard, and the measurement may be performed during production of the paper and/or the cardboard. Thus, the movement of the sheet 10 which is shown by an arrow in Figures may be caused by a paper machine that moves the sheet 10 in a machine direction. A first light source 100 illuminates the sheet 10 while the sheet 10 is moving with respect to the illumination for causing a light spot 102 on the sheet 100 which is also detected and which travels over the sheet 100 while the sheet 100 is moving. The first light source 100 may output visible light in the range of about 400 nm to 750 nm. The output band may also cover wavelengths outside the visible light such as ultraviolet and infrared. The radiation may be temporally continuous light without intentional modulation in the intensity. However, a deliberate modulation is possible. The first light source 100 may output a broad band light where the band is tens to hundreds of nanometers wide or one or more narrow band light where the band is less than tens of nanometers wide. The first light source 100 may comprise one or more incandescent lamps, halogen lamps, gas discharge lamps, leds (light emitting diode), lasers, some combination thereof or the like.

In the example of FIG. 1A, the first light source 100 may control the size of a spot 102 that is detected. The first light source 100 may limit a detectable dimension D of the reflection of the spot 102 on the sheet 10 in the direction of movement by outputting a beam of light whose opening angle α is so narrow that a diameter of the spot 102 on the sheet 10 in the direction of movement of the sheet 10 is as small as or smaller than a lowest acceptable resolution of the measurement in the direction of the movement of the sheet 10. Since the small scale of the measurement determines the lowest acceptable spatial resolution, the smallest resolvable property or object is smaller than a few millimeters. The few millimeters may be defined to be equal to or less than about 10 mm. The lowest acceptable spatial resolution may also be less than one millimeter. The term lowest acceptable spatial resolution may be referred to as a shortest distance between separate points that can still barely be distinguished in the measurement.

The output of the light source 100 may be collimated light whose diameter is practically constant between the light source 100 and the sheet 10. The light output by the light source 100 may also converge towards the sheet 10 such that the spot 102 is small enough to achieve the desired resolution.

A detector 106 forms a total intensity of reflection from the light spot 102 illuminating the moving sheet 100 by each detection. The total power refers to the total power of a full or partial illuminated spot 102 in the acceptance angle β of the detector 106. In this example, the total power detected by the detector 106 comes from the whole spot 102 which is at the same time the illuminated spot and the detected spot. An opening angle β of reception may be such that the detector 106 detects the whole spot 102 formed by the light source 104 with the potential limiter 104. An image of the surface of the sheet 10 is not necessary to be formed by the detector 106.

In general, the detector 106 may comprise one or more detecting elements and it may be based on photovoltaic effect, photoconductive effect or photoemissive effect. The detector 106 may comprise a photodiode of PIN type or avalance type. Irrespective whether one or more detecting elements are used for detection, the detector 106 outputs signal carrying information about the total power of the detected light power. The measurement on the basis of total intensity of reflection from the sheet may be repeated several times for determining a small scale property of the sheet.

Since a detection of change in intensity of light requires a certain integration time for the detector 106, it can be considered that each detection of intensity is performed in a time window longer than a response time of the detector. That is, for each detection the detector 106 integrates the intensity over a certain time window. Every detection includes both a transform of a total power of the light that the detector 106 has received into a signal carrying information about the intensity of the detected light and an output of the signal. The output signal may be electrical, either analog or digital.

The time window of a detection has to be longer than the response time of the detector 106. However, the lowest resolution requires that duration ($T_{DETECTION}$) of each detection is equal to or shorter than the lowest acceptable spatial resolution divided by a speed of the moving sheet. If the detection of intensity takes a longer time, a point on the web 10 moves a longer distance during the detection than the coarsest desired spatial resolution in the direction of the movement of the sheet 10 allows i.e. a few millimeters. Since the response times of semiconductor detectors per se are typically much shorter than the required detection time of the measurement, the total intensity received by the detector 106 may be integrated over a desired time window. The desired time window may be a sliding time window or the time windows may be predeterminately successive. In a digital signal processing samples are taken from a signal. Then each sample has duration equal to or shorter the lowest acceptable spatial resolution divided by a speed of the moving sheet. The samples must also be taken within a time window equal to or shorter the lowest acceptable spatial resolution divided by a speed of the moving sheet.

The integration time of a detector of present technology is around 1 μs or less, for example. Assume now that the web 10 moves with speed 30 m/s, and the required resolution is at least 1 mm. Then the detection time $T_{DETECTION}$ becomes $T_{DETECTION}=(1\ mm)/(30\ m/s)=33\ \mu s$. If, on the other hand, a detection frequency is about 1 MHz i.e. detection time is about 1 μs, the finest achievable spatial resolution is about 30 μm, assuming that the web 10 travels at said speed 30 m/s. All in all, the detection integrates light intensity over the spot 102 in a time window which is fast enough for the small scale measurement of gloss.

Figure 1B:
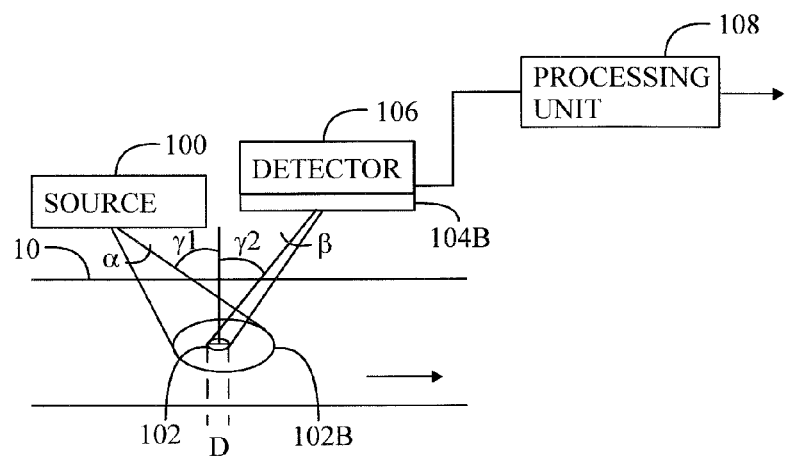

FIG. 1B presents an alternative embodiment of the apparatus of measuring a small scale property of a moving sheet 10. The embodiment resembles the embodiment described in conjunction with FIG. 1A. However, in this embodiment the light source 100 illuminates a wider area 102B on the sheet 10 than that covered by the detection. The detector 106 accepts light from the detected spot 102, which is a part of the illuminated area 102B, for reception. The detector 106 namely has a limited reception angle β that is so narrow that a diameter of the detected spot 102 on the sheet 10 in the direction of movement is as small as or smaller than the lowest acceptable spatial resolution of the measurement. In this example, the total power detected by the detector 106 refers to the total power of a section of the illuminated spot 102B in the solid acceptance angle β of the detector 106. The section in this example is the detected spot 102.

Figure 1C:
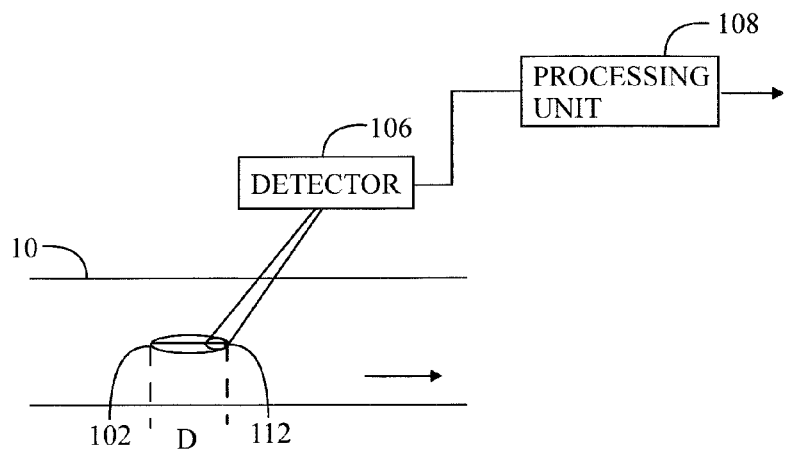

FIG. 1C presents a further alternative embodiment of the apparatus of measuring a small scale property of a moving sheet 10. In this example, the size of the spot 112 observed each moment is smaller than what is required for the lowest spatial resolution. The size of the illuminated spot 112 may also be smaller than what is required for a desired spatial resolution. In this example, the size of the illuminated spot 112 may be limited by the light source 100 with or without the limiter 104 or by the detector 106 with or without the limiter 104B in a manner shown and explained in FIGS. 1A and 1B. During the detection time $T_{DETECTION}$ the sheet 10 moves distance S which may be expressed as S= $T_{DETECTION}*T_{SHEET}$=desired spatial resolution≤the lowest acceptable spatial resolution. Since the size of the spot 112 seen by the detector 106 at one moment is small, the spot 112 as if forms a segment of line which is the detected spot 102 on the web 10 during the detection time window.

In an embodiment, the dimension of the detected spot 102 may be R times larger than the cross section D of the illuminated spot 112 in the direction of movement of the sheet 10, where R is a positive real number. Then the detector 106 may integrate the received reflection from the illuminated spot 112 over the detection time window for outputting the electric signal carrying information about the intensity of the detected spot 102. If one detection takes 10 µs, the speed of the sheet 10 is 20 m/s and a diameter of the illuminated spot 112 is D=20 µm, the illuminated spot 112 moves a distance the length of which corresponds to R=10 times its diameter during the detection time window. The elongated spot 102 formed in this manner may be the basis of one detection of the surface of the sheet 10. Thus, the cross section of the detected spot 102 in the direction of movement may be smaller than the few millimeters for the detector 106 to be able to integrate the total intensity of the reflection over a length of movement S which is longer than a cross section of the illuminated spot 112.

In FIGS. 1A to 1C, the processing unit 108 forms information about a small scale variation of gloss of the sheet 10 on the basis of the total intensities provided by the detector 106. The processing unit 108 may be a computer. The processing unit 108 may comprise at least one processor, memory and at least one suitable computer program for forming the information about the small scale variation of gloss. The processing unit 108 may additionally or alternatively form a small scale gloss of the sheet 10 which is an absolute value with respect to the relative gloss data of the small scale variation of gloss.

Figure 2:
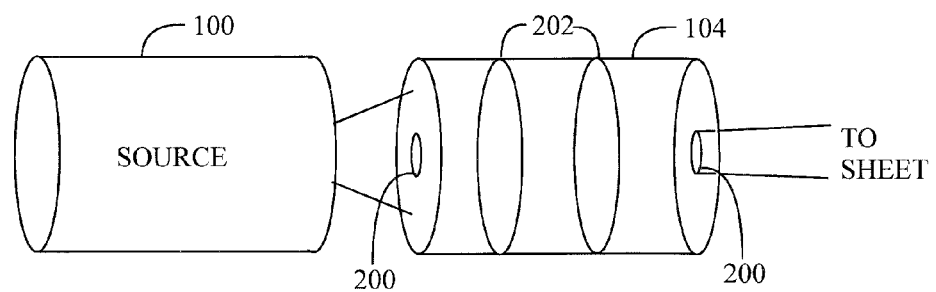
FIG. 2 illustrates an example of an angular limiter of a light source.

FIG. 2 shows an embodiment where an output limiter 104 may be in the front of the light source 100. Alternatively or additionally, the limiter 104 may reside inside the light source 100. The limiter 104, which may be a structural part of the light source 102 or a separate component, may be adjusted such that the diameter of the spot 102 is within the acceptable size. The adjustment of the limiter 104 may be preset during its manufacturing, and/or the adjusting may once or repeatedly be performed before or during each measurement. The limiter 104 may comprise one or more adjustable apertures 200 and one or more optical components 202 such as one or more lenses, one or more mirrors, some of their combination or the like. The one or more lenses and/or the one or more mirrors may be moved with respect to each other or with respect to the light source 100 for adjusting the spot size.

Figure 3:
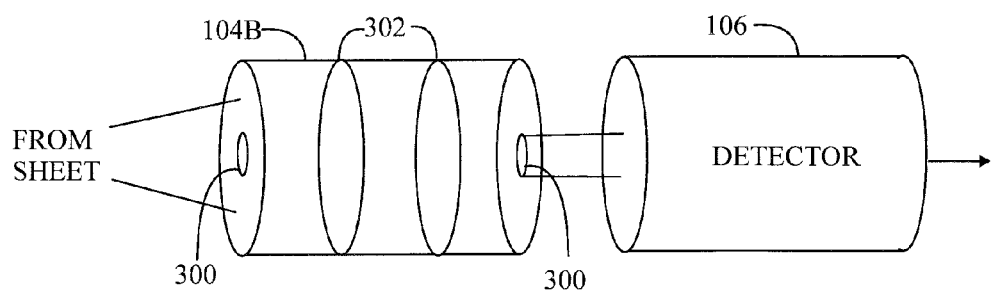
FIG. 3 illustrates an example of an angular limiter of a detector.

FIG. 3 shows an embodiment where a receiver limiter 104B may be inside or in the front of the detector 106. The limiter 104B, which may be a structural part of the detector 106 or a separate component, may be adjusted such that the diameter of the spot 102 is within the acceptable size. The adjustment of the limiter 104B may be preset during its manufacturing, and/or the adjusting may once or repeatedly be performed before or during each measurement. The limiter 104B may comprise one or more adjustable apertures 300, one or more optical components 302 such as one or more lenses, one or more mirrors, some of their combination or the like. The one or more lenses and/or the one or more mirrors may be moved with respect to each other or with respect to the detector 106 for adjusting the detected spot size.

Figure 4:
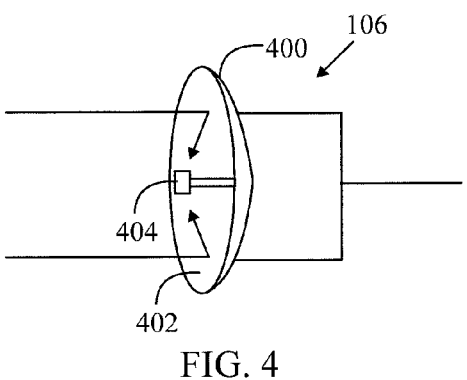
FIG. 4 illustrates an example of non-image forming light collection to a detector.

FIG. 4 shows an embodiment where the detector 106 may collect light from the light spot 102, 112 in a non-image forming manner. The detector 106 as such may have a reflecting cone, hyperboloid or paraboloid structure or the like 400 the inner surface 402 of which reflects light to the at least one detecting element 404 of the detector 106. The reflection may be specular or diffuse. The structure may collect light and limit the reception angle. Alternatively or additionally, the reflecting structure may 400 be a part of the limiter 104B of the detector 106.

Figure 5:
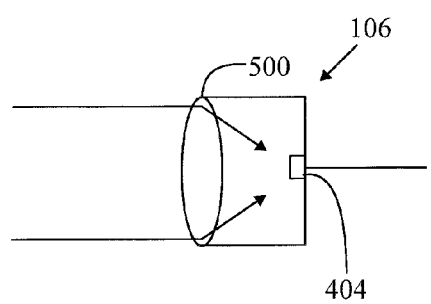
FIG. 5 illustrates an example of image forming light collection to a detector.

FIG. 5 shows an embodiment where the detector 106 may collect light from the light spot 102, 112 to the detector 106 by a lens structure 500. The lens structure 500 may form an image on the at least one detecting element 404 of the detector 106. Instead of forming an image, the lens structure 500 may collect light to the detecting element 404.

In an embodiment, the detector 106 may receive specular reflection of light from the light spot 102, 112, the light being directed to the spot 102, 112 by the light source 100. The light source 100 may direct light to the sheet 100 at a predefined angle between 0° and 90° with respect to the normal of the sheet 10. The normal may mean an average normal measured at several locations when the surface of the sheet 10 is at least approximately in a form of a plain.

In an embodiment, the light source 100 may direct light to the sheet 100 at about an angle γ1 ranging 60° to 75°, for example. However, the angle γ1 may also be different. The direction of a reception angle γ2 of the detector 106 may be the same as that of the light source 100, γ1=γ2, for enabling detection of specular reflection. Instead, the direction of the reception angle of the detector 106 may be different from that of the light source 100, γ1≠γ2, for enabling detection of diffuse reflection.

In an embodiment, the detector 106 may receive diffuse reflection of light from the light spot 102, 112, the light being directed to the spot 102, 112 by the light source 100.

When specular reflection is detected a part of the reflected light may comprise diffuse reflection, too. When diffuse reflection is detected a part of the reflected light may also comprise specular reflection. That may be due to opening angle α of the light source 100 and/or the opening angle β of the detector 106.

Figure 6:
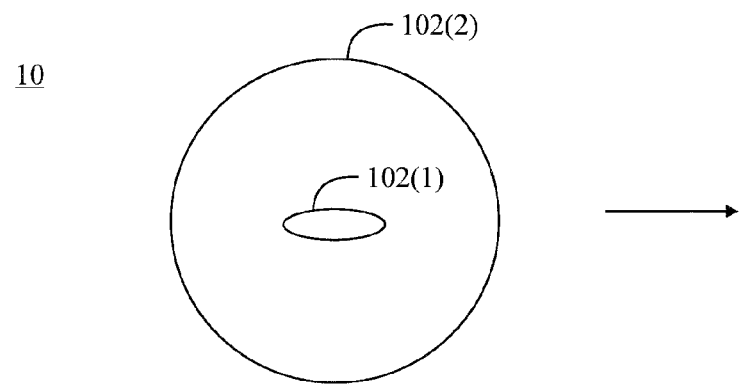
FIG. 6 illustrates an example of use of different spot sizes.

In an embodiment shown in FIG. 6, the size of the detected spot 102 may be varied and/or the measurement may be performed with a plurality of detected spots 102(1) and 102(2) which have different sizes. The difference may be in the area of the detected spot 102(1), 102(2) or in the diameter of the detected spot 102(1), 102(2). The diameter of the detected spot 102(1), 102(2) may be different in the direction of movement of the sheet 10. The detected spot size 102(1), 102(2) may be changed by the first light source 100 or the first detector 106. Alternatively or additionally, the detected spot size 102(1), 102(2) may be changed by the limiters 104, 104B. With spots 102(1), 102(2) having different sizes it may be possible to detect simultaneously at least one common point of the sheet 10. A smaller spot 102(1) may partly or fully be inside a larger spot 102(2), for example. The variation of the detected spot size may be applied also for other light sources and detectors shown in FIGS. 7 and 8. The detected spots 102(1), 102(2) of different sizes may be detected using different wavelengths. The larger the larger detected spot 102(2) is, the more averaged or general gloss result may be formed. If a detected dimension is longer than the lowest acceptable resolution for the small scale measurement, an absolute gloss value may be formed.

Figure 7:
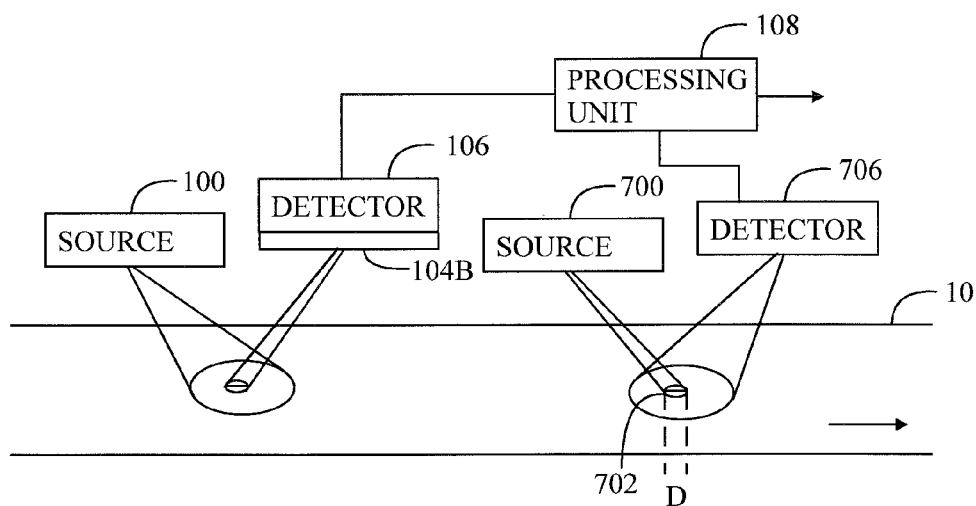
FIG. 7 illustrates an example of a use of different colors in the measurement.

FIG. 7 shows an embodiment where the apparatus may further comprise one or more additional light sources 700. The configuration of FIG. 7 is similar to that of FIG. 1A. Configurations similar to those presented in FIGS. 1B and 1C may be realized but they aren't presented in Figures. Each of light sources 700 may output an additional beam of light in an optical band which has no common wavelength with each other or with the first optical band of the first light source 100. The one or more additional light sources 700 may be directed to the sheet 10 in a similar manner to that of the first light source 100. Also the measurement with the additional light sources 700 and the additional detectors 706 is similar to that with the first light source 100 and the detector 106.

In FIG. 7 the first light source 100 and the first detector 106 have been drawn separately with respect to the additional source 700 and the additional detector 706, respectively. They may be separate but light sources 100 and 700 may be the integrated together or there may only be one common light source 100, 700. Similarly, the additional detector 706 may be separate from the first detector 106 or they may be integrated together or there may only be one common detector 106, 706.

The one or more additional detectors 706 the number of which corresponds to the number of the additional light sources 700 may receive reflections from one or more additional light spots 702 formed on the sheet 100. Each additional detector 700 may perform a detection, in a time shorter than the cross section of a corresponding spot 702 divided by a speed of the sheet 10 in the machine direction. The detection includes both a transform of a total power of the light that the additional detector 706 has received into a signal carrying information about the intensity of the detected light and an output of the signal.

The processing unit 108 may additionally to the measurement with the first light source 100 and the first detector 106 form on the basis of the signaling from the at least one additional detector 706 information about the variation of a small scale gloss of the sheet 10. The small scale gloss is variable due to the movement of the sheet 10 with respect to the one or more additional light spot 702. The processing unit 108 may form a small scale gloss of the sheet 10 in a similar manner to that explained in conjunction with FIGS. 1A to 1C.

In an embodiment, the processing unit 108 may determine an absolute small scale gloss on the basis of electric signaling from the first detector 106 and the one or more additional detectors 706.

Figure 8:
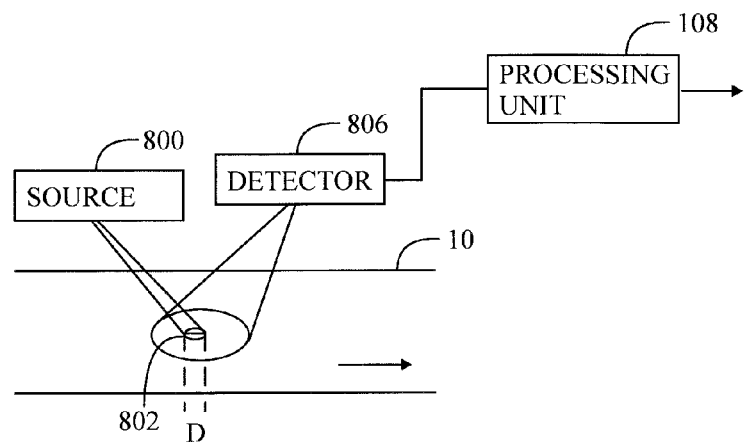
FIG. 8 illustrates an example of a crosswise measurement of gloss.

FIG. 8 shows an embodiment where the apparatus may further comprise one or more auxiliary light sources 800 which may structurally and operationally be similar to the first light source 100 and the additional light sources 700. The first light source 100 and the detector 106 have not been drawn in FIG. 8 for clarity. Each of the light sources 800 may output an auxiliary beam of light at a predefined angle between 0° and 90° with respect to the normal of surface of the sheet 10. A cross section of each auxiliary light spot 802 formable on the sheet 10 may be smaller in a direction of movement than a few millimeters. The one or more auxiliary light sources 800 may be directed to the sheet 10 in a similar manner to that of the first light source 100. Also the measurement with the auxiliary light sources 800 and the additional detectors 806 is similar to that with the first light source 100 and the detector 106.

One or more auxiliary detectors 806 the number of which corresponds to the number of the auxiliary light sources 800 may receive reflections from the one or more auxiliary light spots 802 formable on the sheet 10. Each auxiliary detector 806 may perform a detection, in a predetermined time shorter than the cross section of any auxiliary beam divided by the speed of the movement of the sheet 10 with respect to the at least one auxiliary detector 806.

The one or more auxiliary sources 800 of light and the one or more auxiliary detectors 806 traverse over the sheet 10 for moving the one or more auxiliary light spots 802 over the sheet 10 in a crosswise direction with respect to the movement of the sheet 10.

The processing unit 108 may additionally use the signaling from the one or more auxiliary detectors 806 to form information about the variation of gloss of the sheet 10. The small scale gloss in this embodiment is variable due to the movement of the sheet 10 with respect to the at least one light spot 802. The processing unit 108 may form a small scale gloss of the sheet 10 in a similar manner to that explained in conjunction with FIGS. 1A to 1C.

Figure 9:
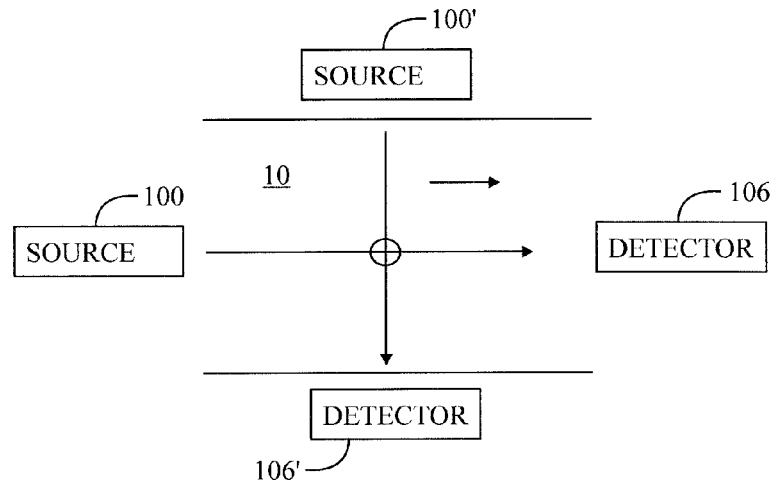
FIG. 9 illustrates an example of simultaneous crosswise and parallel measurement with respect to the movement of the sheet.

In an embodiment shown in FIG. 9, the measurements parallel to the direction of the movement of the sheet 10 and crosswise to the direction of the movement of the sheet 10 may be performed at the same time at the same point of the sheet 10. The light source 100 may output light and the detector 106 may detect the reflection of the light output by the light source 100. The light source 100' may output light and the detector 106' may detect the reflection of the light output by the light source 100'. The angle at which the intensity of the reflection is measured may be the same or different in the parallel and crosswise measurements. Also the sizes of the detected spots may be the same or different. Difference in spot size may be possible particularly if different optical bands are used in the parallel and crosswise measurements.

Figure 10:
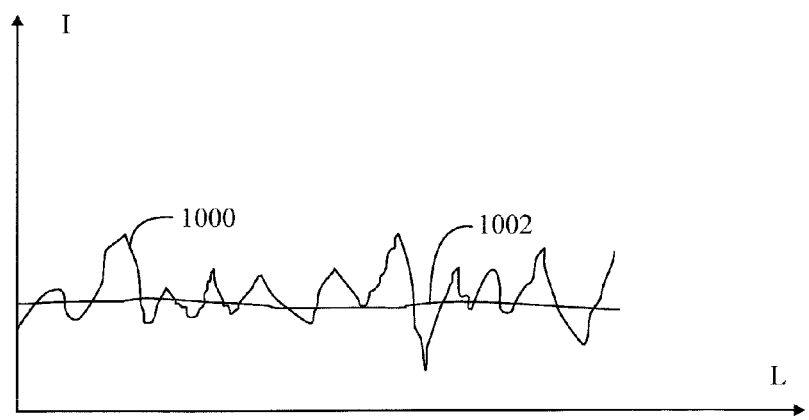
FIG. 10 illustrates an example of a small scale power curve and a larger scale power curve measured by a detector.

FIG. 10 presents intensity curves 1000, 1002 of a detector 106, 706, 806 which represent the variation of intensity of reflection from the sheet 10. The vertical axis refers to intensity I in an arbitrary scale and the horizontal axis refers to measured distance L on the sheet 10. The curve 1000 is measured with a detected spot 102 having a suitable size and a suitable detection time for a small scale measurement. It can be seen that the curve 1000 has a large variation which resembles a random signal. The frequencies in the curve 1000 typically may vary from 1 kHz to 1 MHz, the frequencies and wavelengths carrying information about small scales variation of gloss which depends on surface texture, formation, small scale variation of coating, uneven absorption of ink or the like. Such frequency band, however, is not possible for the present gloss measurement devices having a stroboscopic light and a phase locked detection. The curve 1002 may have been measured with a detected spot the size of which larger than what is suitable for small scale measurement. Hence, the spot size of curve 1002 may be more than one square centimeter and the diameter of the spot may be more than 10 mm in the direction of the movement of the sheet 10. Because the large spot size integrates or averages the variation of the curve, the curve 1002 is much smoother. Alternatively or additionally, the curve 1002 may have been measured with a longer time window for the detection than acceptable for the small scale measurement. Hence, the detection time in conjunction with the curve 1002 is longer than the required spatial resolution for the small scale measurement divided by the speed of the sheet 10. The result may be achieved by sampling the intensity for each detection long enough or by combining samples. The combining may be performed by calculating an average of a plurality of samples of temporally short detections, for instance.

In an embodiment, the processing unit 108 may analyze peak-to-peak values of the curve 1000. The peak-to-peak analysis gives information of peaks of gloss variation. The gloss, in turn, refers to roughness of the surface of the sheet 10. An undesirably rough surface may be due to unsuccessful control of coating, nip pressure, dewatering, dosing of raw materials, chemicals, retention agents, fillers or the like. A general purpose is namely that the gloss of a sheet 10 is constant or at least as close to constant as possible, i.e. the peak-to-peak value should be as small as possible. If it is not, a control action may be performed.

In an embodiment, the processing unit 108 may analyze wavelengths of the curve 1000. The wavelengths refer to sinus signals of different frequencies appearing in the curve 1000. The wavelengths and their percentages in the curve 1000 may be found by Fourier-analysis, for example. The wavelength analysis gives information about the small scale variation of gloss which depends on the structure of the surface of the sheet 10 such as surface texture, formation, coating, absorption of ink etc. The frequency distribution should also be even. If a dominating frequency is found, an analysis may be carried out for determining which sub-process and which actuator might be responsible for the frequency in the gloss variation. A reason may be a vibrating roll, too strong dewatering lifting flocks on the surface of the sheet 10 or the like, for example.

In an embodiment, the processing unit 108 may analyze frequencies and their percentages in the curve 1000. This measurement is similar to wavelength measurement. If a roll vibrates such that is causes a regular change in gloss a wavelength of which may L (L=30 cm for example), it means that its frequency is about v/L ((30 m/s)/(0.3 m=100 Hz), assuming that the sheet travels at speed v=30 m/s.

In an embodiment, the processing unit 108 may form an average value of a predetermined time window of the curve 1000. The average may be formed as a root mean square. The average may give a general gloss value of the sheet 10, for example. Instead of the temporal average, a larger spatial average may be used in a form of a larger spot area in detection. All these results include information about the appearance of the sheet 10 for a person.

In an embodiment, at least one of the following: a first light source, at least one of the additional light sources, at least one of auxiliary light source, may output continuous light.

In an embodiment, at least one of the following: a first light source, at least one of the additional light sources, at least one of auxiliary light source, may output modulated light. The modulation of the at least one light sources may be synchronized with the sampling of the corresponding at least one detector such that an output pulse of light is simultaneous with a detection. When modulated output light is used, the detection may be performed by a phase lock detector and a reference measurement for cancelling drift.

Figure 11A:
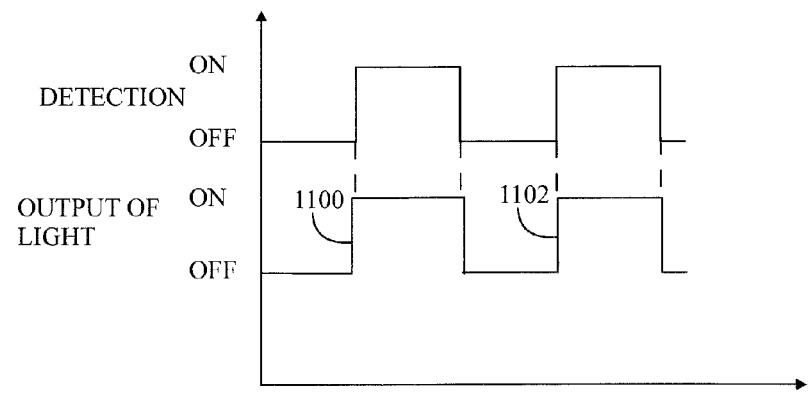
FIG. 11A illustrates an example of modulated measurement.

FIG. 11A presents an example of the synchronized measurement. When a pulse of light is output, the detection may be activated by the rising edge 1100 of the pulse of light. The detection may be switched off predeterminedly before the decaying edge 1102 of the pulse of light. The switching off of the detection may be performed when a predetermined delay has passed after the activation. Alternatively, the detection switch off may be trigged by the decaying edge of the pulse of light. In this way the signal-noise-ratio may be controlled. However, the duration of a pulse of the light doesn't need to be particularly short. For example, the sheet 10 may move during a pulse of light much longer than the lowest spatial resolution i.e. about 10 mm defined by the small scale measurement. The measurement on the basis of total intensity of reflection may be repeated several times for determining a small scale property of a sheet.

Figure 11B:
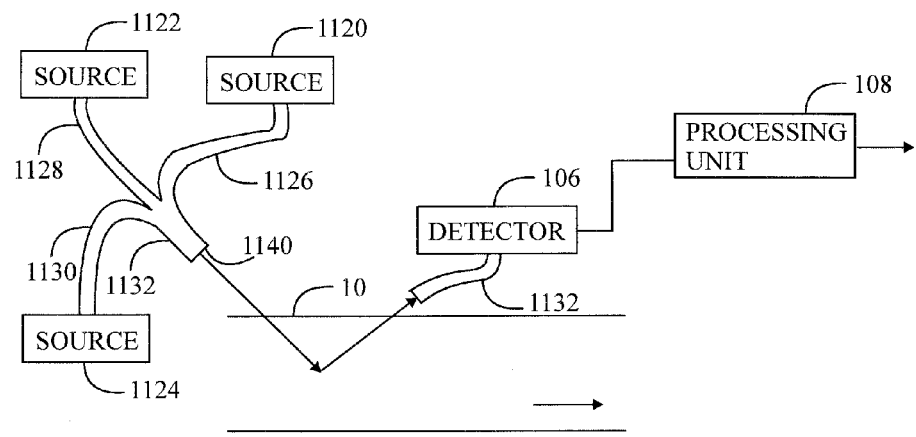
FIG. 11B illustrates an example of pig-tailed light source and detector as well as phase locked detection.

FIG. 11B presents two embodiments. In an embodiment, at least one sub-light source 1120, 1122, 1124 of a light source 106 may be pig-tailed such that each of them comprises an optical fiber 1126, 1128, 1130 the end 1140 of which outputs light towards the sheet 10. In a case of several optical fibers 1126, 1128, 1130, the output of light may be performed through a common fiber 1132 although separate fibers for output may also be possible. In an embodiment, the detector 106 may also comprise a pig-tailed fiber 1132. In an embodiment, at least two sub-light sources 1120, 1122, 1124 may output light in phase locked manner at different frequencies. In processing unit 108, intensities of reflections of the different frequencies may thus be determined separately. If the different sub-sources 1120, 1122, 1124 use different wavelengths or different detected spots 102, different value for gloss may be achieved. In a case of different wavelengths, FIG. 11B is similar to the embodiment described in FIG. 7. A larger detected spot may result in average gloss and a smaller spot 102 may provide information about small scale gloss such as described in conjunction with FIG. 6. Instead of optical fibers, optical radiations from several sub-light sources may be combined by using other optical components such as beam combiners (i.e. beam splitters) deflection mirrors or the like, for example.

Figure 12:
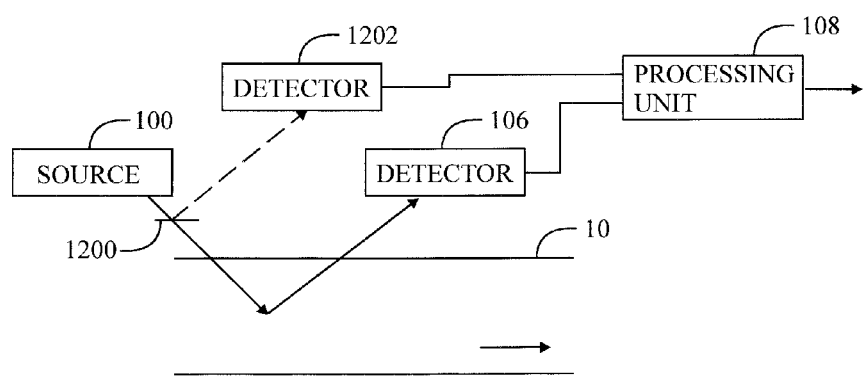
FIG. 12 illustrates an example of reference measurement.

FIG. 12 presents an example of a reference measurement. The beam of light from the first light source 100 may hit a partially transparent mirror 1200 such as a beam splitter before propagating to the sheet 10. The partially transparent mirror 1200 may be a part of the first light source 100. The partially transparent mirror 1200 reflects a known part of the light to a reference detector 1202 which feeds signal carrying information about the intensity of the reference measurement to the processing unit 108. The reference detector 1202 may also be a part of the first light source 100. Since the first detector 106 also feeds its signal carrying information about the intensity of the reflection to the processing unit 108, the processing unit 108 may cancel the effect of a drift of the intensity of the first light source 100 in the measurement. A similar reference measurement arrangement is possible also for other light source 700, 800 and detector 706, 806 pairs presented in FIGS. 7 and 8.

In an embodiment, the first detector 106, at least one additional detector 706 and/or at least one auxiliary detector 806 may comprise an optical fiber for receiving the reflection from the sheet 10.

In an embodiment, the first light source 100, at least one additional light source 700 and/or at least one auxiliary light source 800 may comprise an optical fiber for outputting light to the sheet 10. The opening angle α of the light source 100, 700, 800 may be determined by a numerical aperture of the fiber, for example. Correspondingly, the reception angle β of the detector 106, 706, 806 may be determined by a numerical aperture of the fiber, for example.

Figure 13:
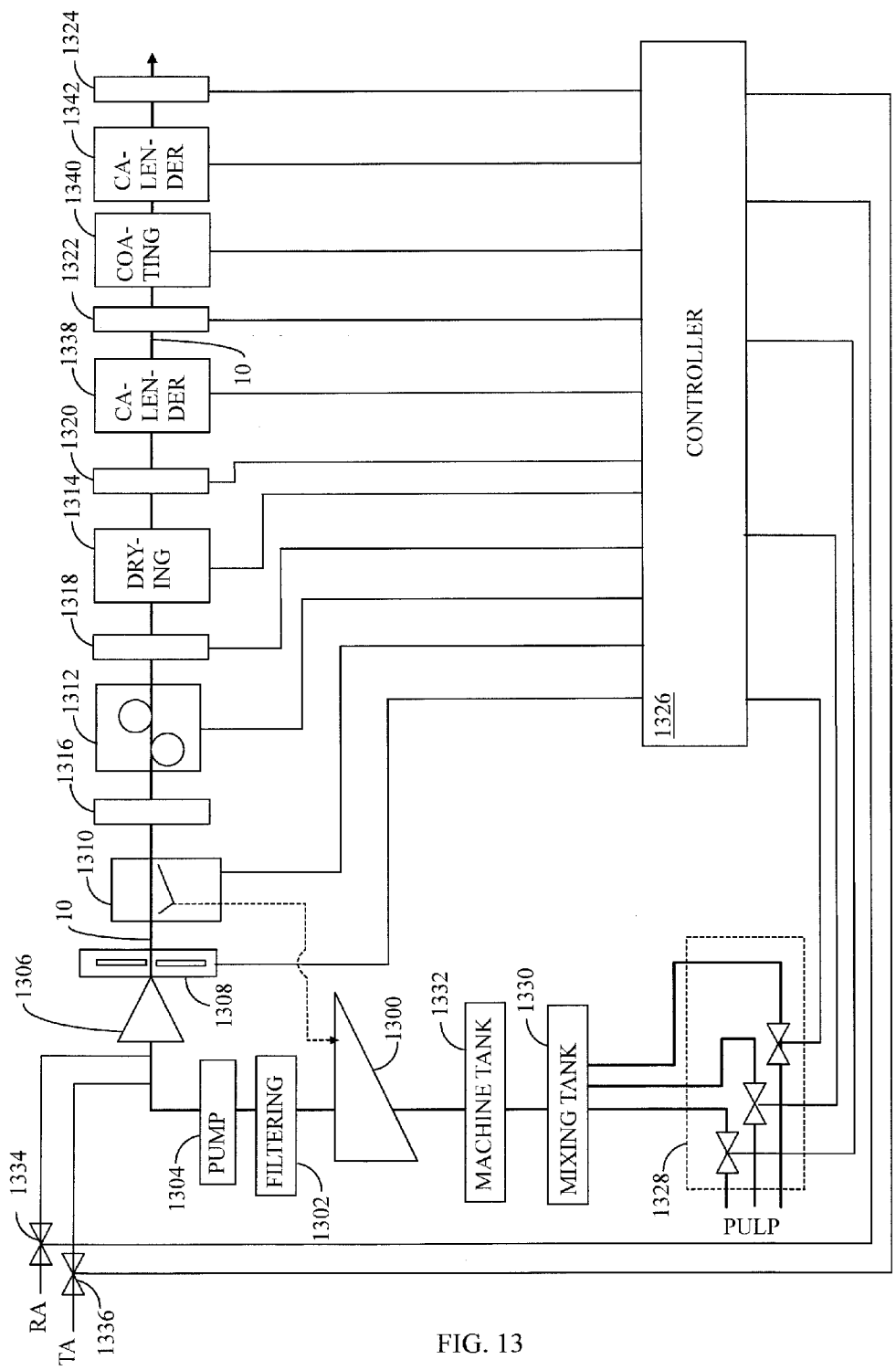
FIG. 13 illustrates an example of a paper machine.

FIG. 13 shows the principle structure of a paper machine. A pulp flow or a plurality of pulp flows may be fed into the paper machine through a wire pit 1300, which is usually preceded by a mixing tank 1330 for pulp flows and a machine tank 1332. The pulp may contain coloring substances which may be traces of coloring substances from colored paper or recycled paper added to the pulp on purpose. Machine pulp is batched for a short circulation by a weight control or a grade change program. The mixing tank 1330 and the machine tank 1332 may also be replaced by a separate mixing reactor (not shown in FIG. 13) and the batching of machine pulp is controlled by feeding each pulp flow separately by means of valves or some other flow regulating means 1328. In the wire pit 1300, the machine pulp is mixed with water to provide the short circulation (a broken line from a former 1310 to the wire pit 1300) with a desired consistency. From the pulp thus produced, it is possible to remove sand (hydrocyclones), air (deaeration tank) or other rough material (pressure screen) by cleaning equipment 1302, and pulp is pumped by means of a pump 1304 into a head box 1306. Before the head box 1306, if desired, a filler TA, such as kaolin clay, calcium carbonate, talc, chalk, titanium oxide, silica, etc., and/or a retention agent RA, such as inorganic, natural organic or synthetic water-soluble organic polymers may be added to the pulp. The filler may have effect on gloss, formation, surface properties, opacity, brightness and printability and to reduce manufacturing costs. The retention agents RA, for their part, increase the retention of fines and fillers and simultaneously speed up the dewatering in a manner known per se. Both the fillers and the retention agents affect the surface topography of the web and the paper and can thus have effect on gloss. With TA and/or RA at least one coloring substance may be added to the pulp.

From the head box 1306, the pulp is fed through a slice 1308 of the head box into the former 1310, which may be a fourdrinier or a gap former. In the former 1310, the web 10 is dewatered and ash, fines and fibres are removed into the short circulation. In the former 1310, the pulp is fed as a web 10 onto the wire, and the web 10 is preliminarily dried and pressed in a press 1312. The web 10 is primarily dried in a drying section 1314. There is usually at least one measuring part 1316 to 1324, by which for instance the gloss variation of the web 10 can be measured.

A paper machine, which in this application refers to both paper and cardboard machines, may also comprise, for instance, a precalender 1338, a coating part/section 1340 and/or a post-calender 1342. However, a coating section 1340 is not necessary, and in that case more than one calender 1338, 1342 is not needed. In the coating section 1340, a coating colour, which may contain for example kaolin, chalk or carbonate, starch, and/or latex, may be applied onto the paper surface. The use of coating colour usually reduces the roughness of the paper and improves gloss.

In the calenders 1338, 1342, in which an uncoated or coated paper web travels between rolls that press with a desired force, the surface topography of the paper, such as roughness, can be changed. Hence, the calender 1338, 1342 may also be used to change the thickness and/or gloss of the paper. In the calender 1338, 1342, the properties of the paper web may be changed by moistening the web or by means of temperature and nip load/pressure between the rolls so that the greater the press applied to the web is, the smoother and glossier the paper will become. Moistening and an increase in the temperature further reduce roughness and improve gloss. In addition, it is obvious that the operation of a paper machine is known per se to a person skilled in the art, wherefore it is not described in more detail in this context.

FIG. 13 also shows a control system for the paper machine. A controller 1326 may control the batching of pulp flows by means of regulating valves 1328, the batching of the filler TA by a valve 1336, the batching of the retention agent RA by a valve 1334, it may also control the size of the slice 1308, the machine velocity, the amount of backwater and the drying process in block 1314. The control actions of the controller 1326 are based on the measuring devices 1316 to 1320 which comprise at least one detector 106, 706, 806 and at least one light source 100, 700, 800 for measuring gloss variation and also potentially the absolute gloss. The controller 1326 may also measure the web 10 properties elsewhere (e.g. at the same points where controls are carried out).

The controller 1326 may be considered as a control arrangement based on automatic data processing of the paper machine, or as a part thereof. The controller 1326 may receive digital signals or convert the received analog signals to digital signals. The controller 1326 may comprise a microprocessor and memory and process the received signals according to a suitable computer program. The controller 1326 may be based on a PID (Proportional-Integral-Derivative), MPC (Model Predictive Control) or GPC (General Predictive Control) control, for example.

In an embodiment, the controller 1326 may optimize the process on the basis of the gloss measurement presented in this application. The controller 1326 may control at least one actuator of a process producing the sheet on the basis of the information of the small scale variation of gloss which is formed in the processing unit 108. The controller 1326 may control at least one of the following: the formation by regulating the head box 1306, the amount of raw materials by regulating the valves 1328, amount of chemicals by regulating the valves 1334, 1336, the formation and the dewatering by regulating the former 1310, the roughness of sheet 10 by regulating the pressure of the press 1312, the surface texture and roughness of the sheet 10 by regulating drying power of the drying 1314, the nip pressure of the calendar 1338, the coating process in the coating section 1340, the nip pressure of the calendar 1342, the tension of the sheet 10. For example, addition of kaolin and/or coating pigments may increase gloss of the sheet 10. Similarly, steam ironing may increase gloss. Addition of calcium carbonate may in turn decrease gloss.

The processing unit 108 may be a part of the controller 1326 or a separate data processor.

Figure 14:
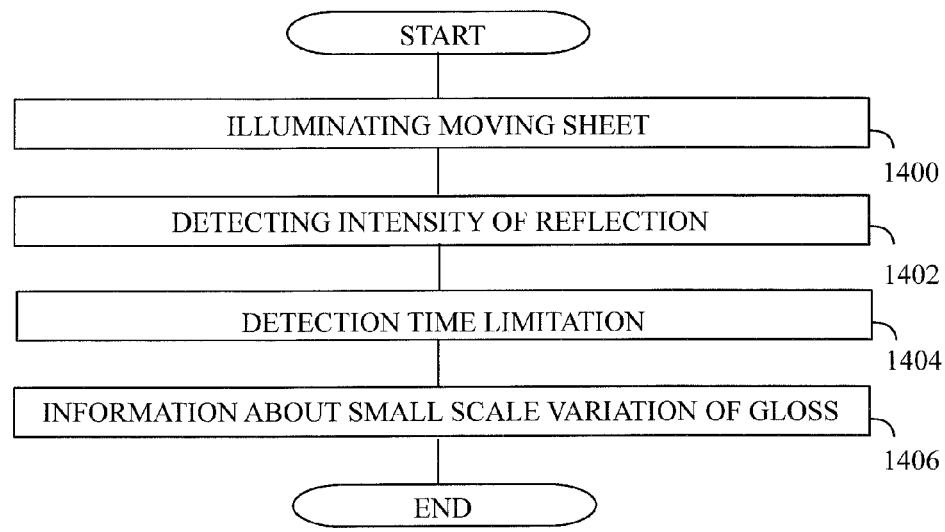
FIG. 14 illustrates an example of a flow chart of a measurement method.

FIG. 14 presents a flow chart of the measuring method. In step 1400, a first light source illuminates the sheet moving with respect to the illumination. In step 1402, a detector forms a total intensity of reflection of the light illuminating the moving sheet by each detection, where a detected dimension (D) of the reflection on the sheet in the direction of the movement being limited the same as or shorter than a lowest acceptable spatial resolution of the measurement. In step 1404, a duration ($T_{DETECTION}$) of each detection is kept equal to or shorter than the lowest acceptable spatial resolution divided by a speed of the moving sheet. In step 1406, processing unit forms information about a small scale variation of gloss of the sheet on the basis of the detections by the detector.

Figure 15:
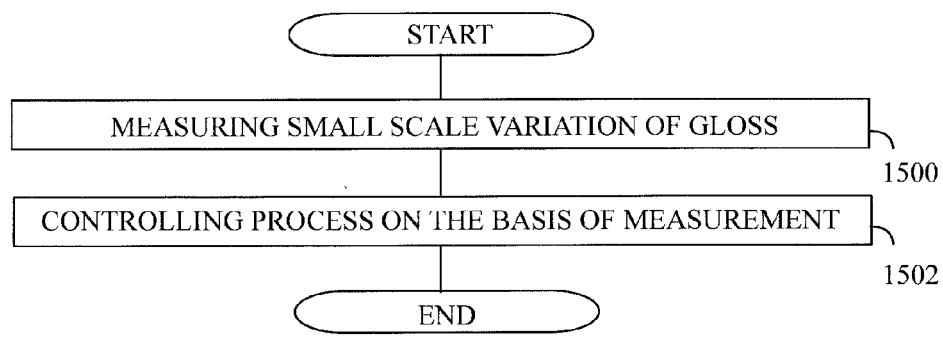
FIG. 15 illustrates an example of a flow chart a control method.

FIG. 15 presents a flow chart of the control method. In step 1500, steps of flow chart 14 are performed. In step 1502, a controller controls at least one actuator of a process producing the sheet on the basis of the information about the small scale variation of gloss.

In an embodiment, the aspects of the invention may be realized as software and a computer or a set of computers of the processing system or a web service system connected to Internet.

The computer programs may be in source code form, object code form, or in some intermediate form, and it may be stored in some sort of carrier, which may be any entity or device capable of carrying the program. Such carriers include a record medium, computer memory, read-only memory, and software distribution package, for example. Depending on the processing power needed, the computer program may be executed in a single electronic digital controller or it may be distributed amongst a number of controllers.

It will be obvious to a person skilled in the art that, as technology advances, the inventive concept can be implemented in various ways. The invention and its embodiments are not limited to the examples described above but may vary within the scope of the claims.

The invention claimed is:

1. An apparatus of measuring a small scale property of a sheet, the apparatus comprising:
   a first light source comprises at least one of the following: led and laser, and the first light source is configured to illuminate the sheet moving with respect to the illumination;
   a detector configured to form a total intensity of reflection of the light illuminating a detected spot on the moving sheet by each detection;
   a detected dimension of the reflection of the spot on the sheet in the direction of the movement being limited the same as or shorter than a lowest acceptable spatial resolution of the measurement;
   a duration of each detection being equal to or shorter than the lowest acceptable spatial resolution divided by a speed of the moving sheet; and
   at least one processor configured to form information about a small scale variation of gloss of the sheet on the basis of the detections by the detector.

2. The apparatus of claim 1, wherein the first light source comprises an output limiter configured to limit a first beam of light with an opening angle for causing a cross section of a light spot of light on the sheet during measurement to be shorter than a few millimeters in the direction of movement for limiting the detected dimension of the reflection.

3. The apparatus of claim 1, wherein the detector comprises a receiver limiter configured to limit the detected dimension in the direction of movement on the sheet by having a limited angle of reception for the detections.

4. The apparatus of claim 1, wherein the dimension of the first beam in the direction of movement being smaller than the lowest acceptable spatial resolution for the detector to be able integrate the total intensity of the reflection over a length of movement longer than a cross section of the light spot from the moving sheet.

5. The apparatus of claim 1, wherein the detected dimension is R times larger than the cross section of the first beam in the direction of movement of the sheet, where R is a positive real number, and the detector is configured to integrate the received reflection over a predetermined time for detection, where the predetermined time is detected dimension divided by the speed of the sheet.

6. The apparatus of claim 1, wherein the detector is configured to receive light from the reflection in a predetermined opening angle including specular reflection.

7. The apparatus of claim 1, wherein the apparatus further comprising one or more additional light sources each of which being configured to output an additional beam of light in an optical band which have no common wavelength with each other or with the first optical band for illuminating the sheet moving with respect to the additional illumination;
   one or more additional detectors, the number of which corresponds to the number of the additional light sources, each being configured form a total intensity of reflection of the additional light by each detection;
   a detected dimension of each additional reflection on the sheet in the direction of the movement being limited the same as or shorter than the lowest acceptable spatial resolution of the measurement;
   a duration of each detection of each additional reflection being equal to or shorter than the lowest acceptable spatial resolution divided by a speed of the moving sheet; and
   the at least one processor being configured to form information about the small scale variation of gloss of the sheet on the basis of the detections by the one or more additional detectors.

8. The apparatus of claim 7, wherein the at least one processor is configured to determine an absolute small scale gloss on the basis of detections from the first detector and the one or more additional detectors.

9. The apparatus of claim 1, wherein at least one of the following: a first light source, at least one of the additional light sources, at least one of auxiliary light sources, is configured to output continuous light.

10. The apparatus of claim 1, wherein at least one of the following: a first light source, at least one of the additional light sources, at least one of auxiliary light sources, is configured to output modulated light.

11. The apparatus of claim 1, wherein the at least one processor comprises
    at least one non-transitory memory including computer program code,
    the at least one non-transitory memory with the at least one processor and the computer program code being configured to cause the at least one processor to form information about the variation of small scale gloss of the sheet.

12. A non-transitory computer program distribution medium readable by a computer and encoding a computer program of instructions for executing a computer process carrying out the forming of the information according to claim 11.

13. A method of measuring a small scale property of a sheet, the method comprising:
    illuminating, by a first light source which comprises at least one of the following: led and laser, the sheet moving with respect to the illumination;
    forming, by a detector, a total intensity of reflection of the light illuminating the moving sheet by each detection, where a detected dimension of the reflection on the sheet in the direction of the movement being limited the same as or shorter than a lowest acceptable spatial resolution of the measurement;
    limiting a duration of each detection equal to or shorter than the lowest acceptable spatial resolution divided by a speed of the moving sheet; and
    forming, by at least one processor, information about a small scale variation of gloss of the sheet on the basis of the detections by the detector.

14. A method of controlling gloss of a moving sheet, the method comprising: controlling, by a controller, at least one actuator of a process producing the sheet on the basis of the information about the small scale variation of gloss formed in claim 13.

15. A process apparatus of controlling gloss of a moving sheet in a process comprising
    at least one actuator;
    at least one processor; and
    at least one non-transitory memory including computer program code,
    the at least one non-transitory memory with the at least one processor and the computer program code being configured to cause the apparatus to control the at least one actuator of the process producing the sheet on the basis of the information of the small scale variation of gloss formed in claim 1.

16. A non-transitory computer program distribution medium readable by a computer and encoding a computer program of instructions for executing the computer process of claim 13.

\* \* \* \* \*